(12) United States Patent
Kalogris et al.

(10) Patent No.: US 10,881,904 B2
(45) Date of Patent: Jan. 5, 2021

(54) POWER STEPPER APP

(71) Applicants: Dimitrios Kalogris, Toronto (CA); Peter Kalogris, Toronto (CA)

(72) Inventors: Dimitrios Kalogris, Toronto (CA); Peter Kalogris, Toronto (CA)

(*) Notice: Subject to any disclaimer, the term of this patent is extended or adjusted under 35 U.S.C. 154(b) by 616 days.

(21) Appl. No.: 15/782,727

(22) Filed: Oct. 12, 2017

(65) Prior Publication Data

US 2019/0111313 A1 Apr. 18, 2019

(51) Int. Cl.
*A63B 24/00* (2006.01)
*A61B 5/11* (2006.01)
*A61B 5/00* (2006.01)
*G01C 22/00* (2006.01)

(52) U.S. Cl.
CPC ........ *A63B 24/0003* (2013.01); *A61B 5/1118* (2013.01); *A61B 5/6828* (2013.01); *G01C 22/006* (2013.01); *A61B 2562/0219* (2013.01); *A63B 2208/0228* (2013.01); *A63B 2220/17* (2013.01); *A63B 2220/64* (2013.01); *A63B 2220/803* (2013.01); *A63B 2220/836* (2013.01); *A63B 2225/50* (2013.01)

(58) Field of Classification Search
CPC . G01C 22/006; A63B 24/0003; A63B 5/1118; A63B 5/6828; A63B 2562/0219; A63B 2208/0228; A63B 2220/17; A63B 2220/64; A63B 2220/803; A63B 2220/836; A63B 2225/50
See application file for complete search history.

(56) References Cited

U.S. PATENT DOCUMENTS

| 9,532,734 | B2 | 1/2017 | Hoffman | |
|---|---|---|---|---|
| 2012/0283855 | A1* | 11/2012 | Hoffman | A63B 24/0021 700/91 |
| 2013/0274587 | A1* | 10/2013 | Coza | A61B 5/0002 600/409 |
| 2017/0136297 | A1* | 5/2017 | Penie | A61B 5/746 |
| 2017/0225032 | A1* | 8/2017 | Jones | A63B 71/141 |

OTHER PUBLICATIONS

Pernek et al. ("Exercise repetition detection for resistance training based on smartphones", see attached publication). (Year: 2012).*

* cited by examiner

*Primary Examiner* — Xin Y Zhong
(74) *Attorney, Agent, or Firm* — Argus Intellectual Enterprise; Jordan Sworen; Daniel Enea

(57) ABSTRACT

A system designed for exercising while sitting includes a rigid housing configured to receive at least one sensor to detect motion. The sensor is configured to identify an oscillatory motion of a knee raising and lowering through pivoting of an ankle of a user wherein a heel of a foot of the user lifts off of a surface and wherein a toe of the user remains planted on the surface. A mobile device in wireless communication with the motion sensor runs an application that provides a user with a multitude of features. The features include exercise statistics, energy spent, and steps taken. A further feature of the mobile device application is to provide a user with a virtual environment on the screen of the mobile device. Exercise performed by the user is translated into forward motion in the provided virtual environment.

17 Claims, 5 Drawing Sheets

POWER STEPPER APP

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of exercise systems of existing art and more specifically relates to mobile device exercise systems.

RELATED ART

Typical pedometer systems rely on a user to actively run or walk long distances. These systems assume a user has convenient access to a treadmill or a facility suitable for running. It is known that running is hard on the joints and feet, especially if the person has pre-existing conditions. Running is not a healthy option for many people. Our elderly population is often advised against running or performing strenuous activity. The population of people with limited mobility is increasing every day and very few exercise techniques are available for them. Here the power stepper app provides a system for the ever-increasing population with limited mobility to exercise from the comfort of their own chair. Users may take an exciting sightseeing virtual tour of many popular destinations while performing an impact free exercise from a seated position. This system aims to provide an effective means to keep motivated and stay active.

U.S. Pat. No. 9,532,734 to Michael T. Hoffman relates to monitoring fitness using a mobile device. The described monitoring of fitness using a mobile device includes athletic performance monitoring and tracking that may provide multiple ways in which to track athletic movement and activity. Workouts may also be tagged with various parameters including mood, weather, terrain, athletic equipment, friends used and the like. Workout information may be shared to social messaging and networking outlets. Workout information shared may include map information including images of maps, interactive maps, links to maps, route information and the like and/or combinations thereof.

SUMMARY OF THE INVENTION

In view of the foregoing disadvantages inherent in the known mobile device exercise system art, the present disclosure provides a novel system designed for exercising while sitting. The general purpose of the present disclosure, which will be described subsequently in greater detail, is to provide an efficient and effective system designed for exercising while sitting.

A system designed for exercising while sitting is disclosed herein. The system is designed for exercising while sitting and includes a rigid housing having a first side and a second side configured to receive at least one piece of motion sensing hardware. At least one sensor is configured to identify an oscillatory motion of a knee raising and lowering (rotating motion about an axis) through pivoting of an ankle of a user wherein a heel of a foot of the user lifts off a surface and wherein a toe of the user remains planted on the surface. A mobile device in wireless communication with the at least one sensor and a mobile device application on the mobile device is configured to: register user to a mobile device application; calibrate strokes of oscillatory motion to a cycle counter of mobile device application; calculate energy expended by the user from performing the oscillatory motion; and display a virtual environment.

According to another embodiment, a method of use for exercising while sitting is also disclosed herein. The method for exercising while sitting includes providing a system designed for exercising while sitting, as described above; attaching a housing with the at least one sensor onto a knee of the user; executing the mobile device application on a mobile device; registering a profile with an online-database such that the user may review and resume progress from a saved point; calibrating the oscillatory motion of the knee of the user such that the at least one sensor records the desired amplitude of motion; choosing the virtual environment to transverse; and exercising through initiation of repetitive oscillatory motion.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a system designed for exercising while sitting, constructed and operative according to the teachings of the present disclosure.

The various embodiments of the present invention will hereinafter be described in conjunction with the appended drawings, wherein like designations denote like elements.

DETAILED DESCRIPTION

Figure 1:
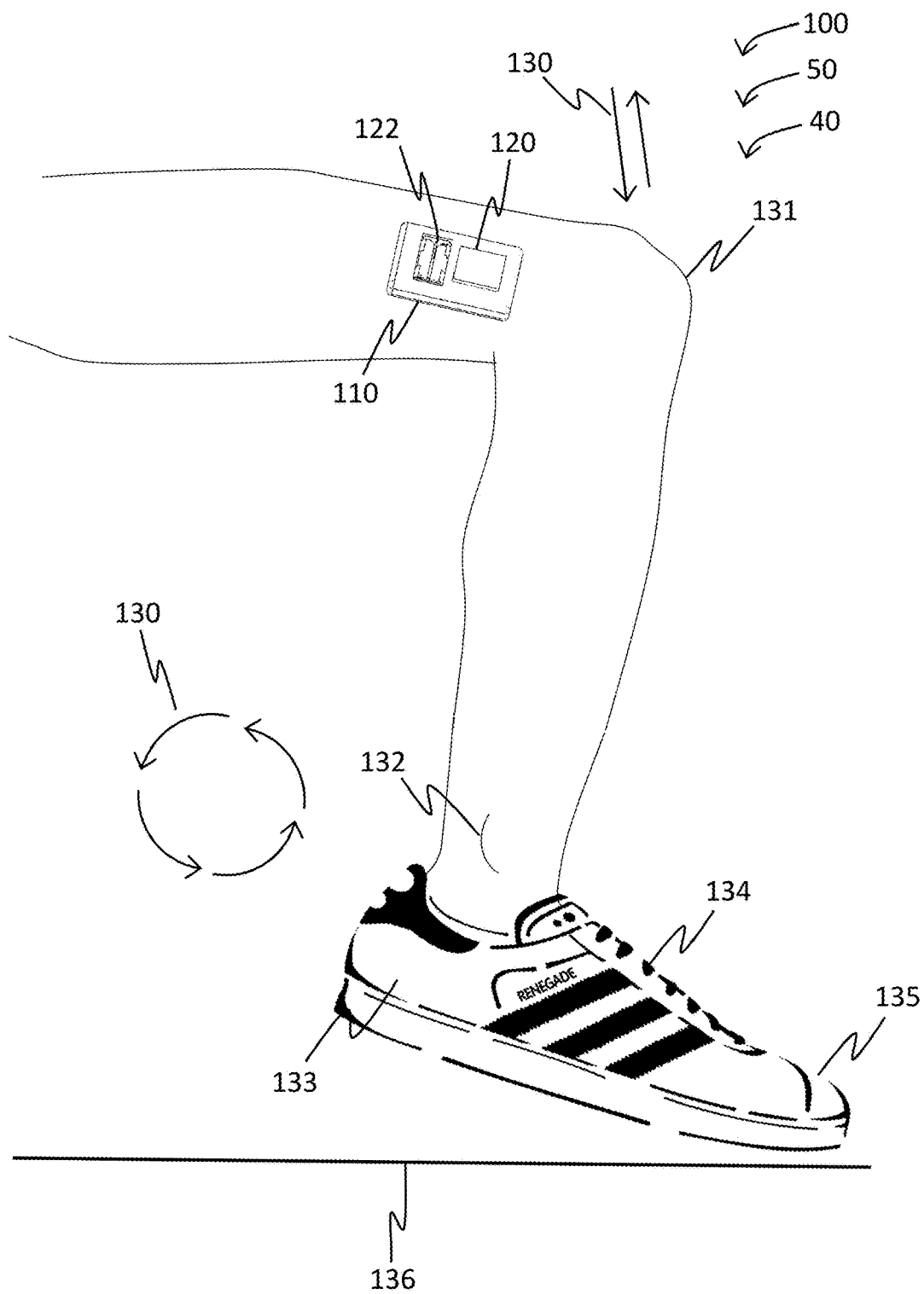
FIG. 1 is an in use view of the system designed for exercising while sitting during an 'in-use' condition, according to an embodiment of the disclosure.

As discussed above, embodiments of the present disclosure relate to mobile device exercise systems and more particularly to a system designed for exercising while sitting as used to improve exercising while sitting techniques.

Generally, the system designed for exercising while sitting comprises a device having a rigid housing configured to receive at least one piece of motion sensing hardware. The rigid housing includes a fastening system disposed across one face for securing the housing on an article of apparel. Fastening systems may include hook and loop, magnetic, spring force clips, pin and hook; further fastening systems may be contemplated.

The housing may be made of a hard plastic or resin and of suitable toughness to withstand frequent handling; wherein the housing includes an aperture configured to fit a USB head. At least one sensor along with a rechargeable power source may be housed within the rigid housing. The sensors are configured to sense and record acceleration and elevation and report the data wirelessly to an internet connected mobile device. The sensor units are configured to identify an oscillatory motion of a knee raising and lowering through pivoting of an ankle of the user; wherein a heel of a foot of the user lifts off of a surface and wherein a toe of the foot of the user remains planted on the surface. This oscillatory motion is the primary exercise technique performed by a user for this system designed for exercising while sitting. The mobile device may be any such device configured with a processor and a memory storage configured to receive a set of commands in the form of an executable application. The device may be a conventional smartphone, tablet or any device encompassed by the IoT having a digital display screen and running an operating system such as Android or iOS.

The mobile device preferably has wireless functionality capable of communicating with the sensors through BLUETOOTH or other similar wireless radio wave communication. A mobile application is included in this system and installed on the mobile device. The mobile application is in communication to an online internet database where a user will register a profile. The users profile may include a plurality of personal details, weight loss goals and a diet plan, which may be accessed through the program or through a web browser external to the mobile device application. The mobile application receives information regarding the user's performance of the oscillatory motion exercise technique from the sensors. Statistical data such as calories burned, rate of oscillation and distance traveled is presented to the user through the digital display on the mobile device. A user may choose from a selection of virtual terrains to traverse such as vacation destinations or commonly toured areas around the globe. The frequency of oscillatory motion performed by the user is translated into a virtual linear velocity for traversing a virtual world displayed on the digital display of the mobile device. The user may then perform the exercise and explore the virtual terrain provided by the online database.

Referring now more specifically to the drawings by numerals of reference, there is shown in FIGS. 1-4, various views of a system designed for exercising while sitting 100.

FIG. 1 shows a system designed for exercising while sitting 100 during an 'in-use' condition 50, according to an embodiment of the present disclosure. Here, the system designed for exercising while sitting 100 may be beneficial for use by a user 40 to burn calories without moving from a resting position. As illustrated, the system designed for exercising while sitting 100 may include at least one sensor 120 and an electronically coupled energy source 122 nested within a rigid housing 110. In a functioning embodiment, the sensor 120 and rigid housing 110 assembly is affixed to the knee 131 of a user 40. The sensor 120 is configured to detect an oscillatory motion 130 of a knee 131 raising and lowering repeatedly. The oscillatory motion 130 is effected by user 40 through the repeated raising of knee 131 and lifting of heel 133 of foot 134 off of surface 136 while keeping toe 135 of foot 134 planted on surface 136.

Figure 2:
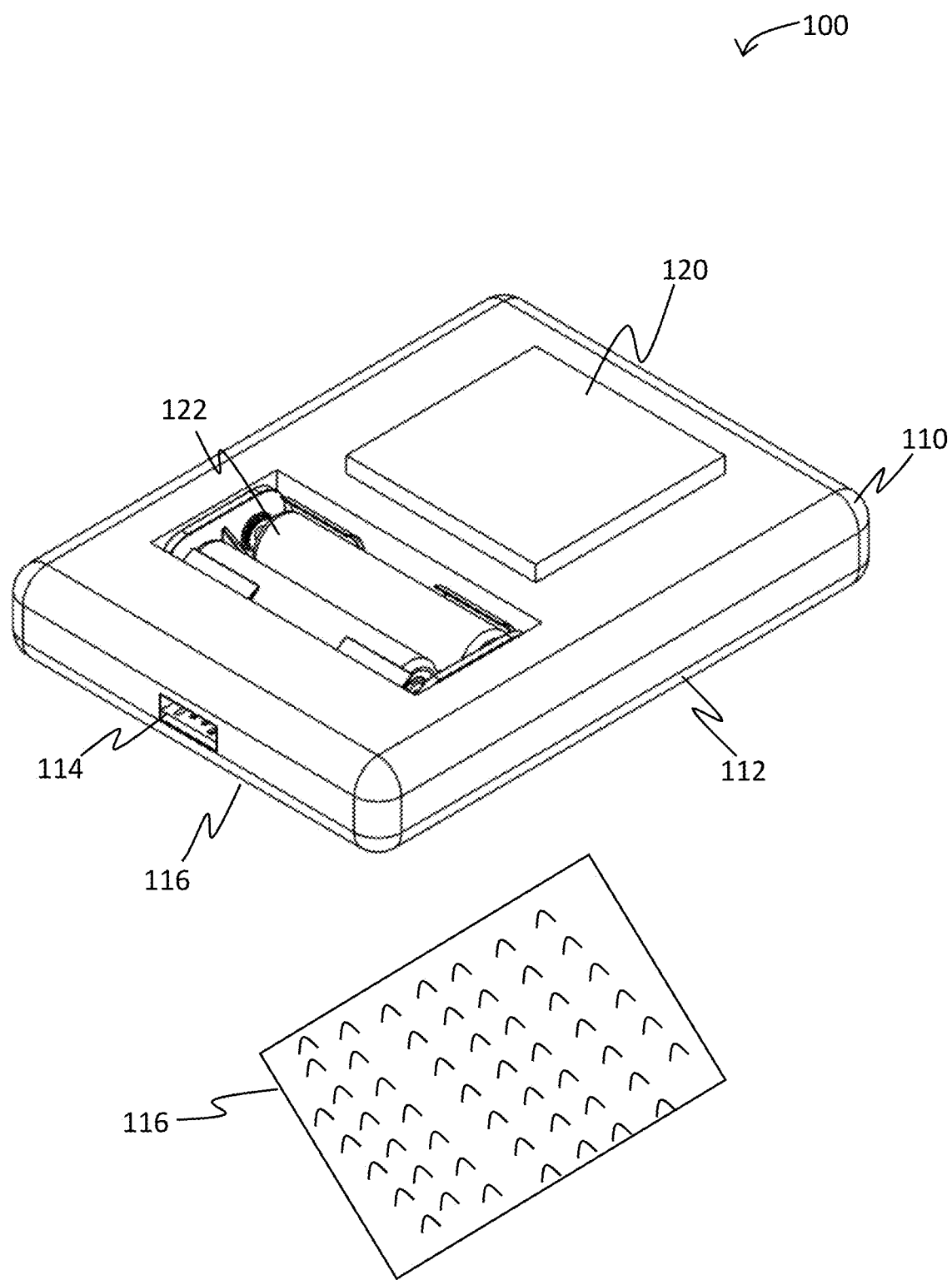
FIG. 2 is another view of the system designed for exercising while sitting of FIG. 1, according to an embodiment of the present disclosure.

FIG. 2 shows the system designed for exercising while sitting 100 of FIG. 1, according to an embodiment of the present disclosure. As above, the system designed for exercising while sitting 100 may include a sensor 120 energy source 122 and rigid housing 110 assembly that is designed to be secured using a hook and loop fastener system 116 that is coupled to a first side 112 of the rigid housing 110. An aperture 114 sized to receive a USB head is located on the rigid housing 110 for charging the included energy source 122 for the sensor 120 unit.

Figure 3:
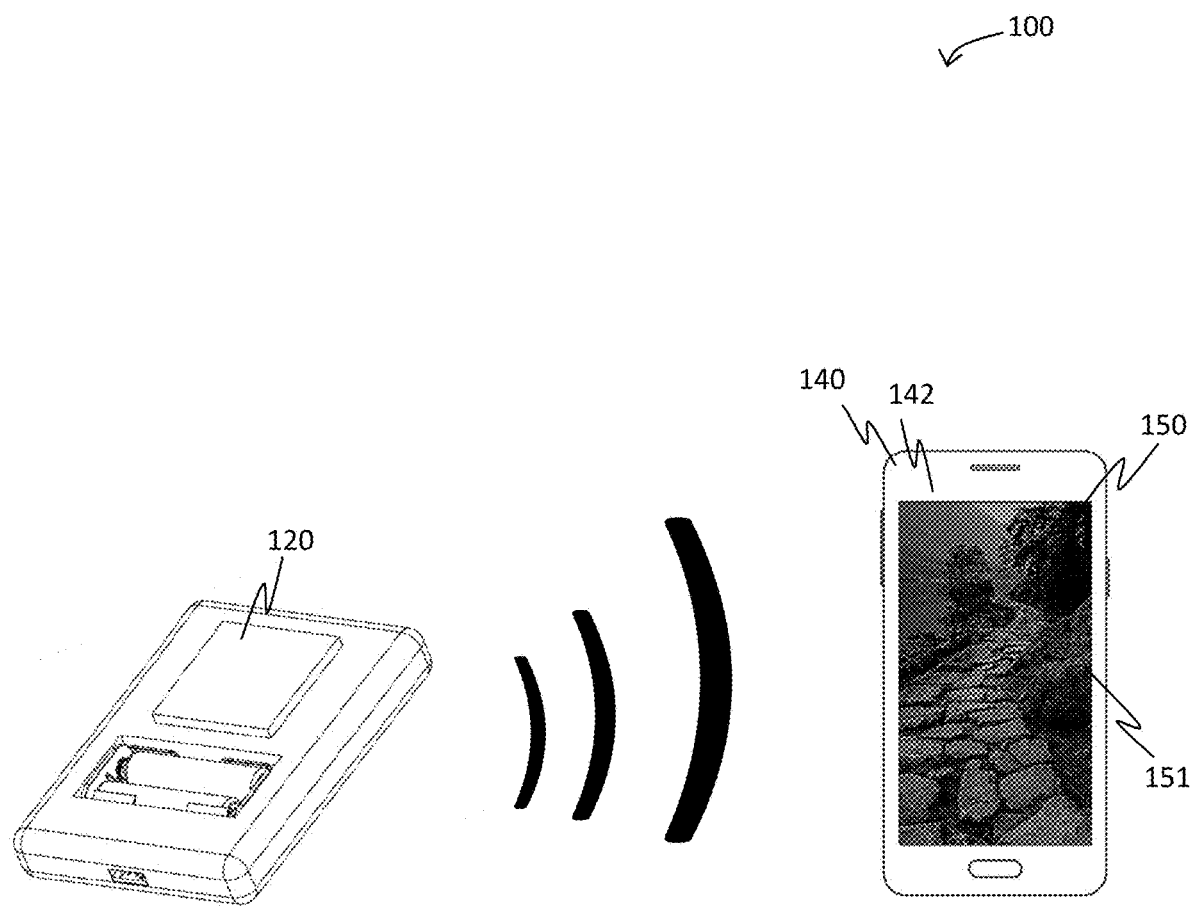
FIG. 3 is another view of the system designed for exercising while sitting of FIG. 1, according to an embodiment of the present disclosure.

FIG. 3 is another view of the system designed for exercising while sitting 100 of FIG. 1, according to an embodiment of the present disclosure. Here a mobile device 140 hosts a mobile device application 150. The mobile device 140 is in wireless communication with the sensor 120 and displays a virtual environment 151 on the digital display 142 of the mobile device 140.

Figure 4:
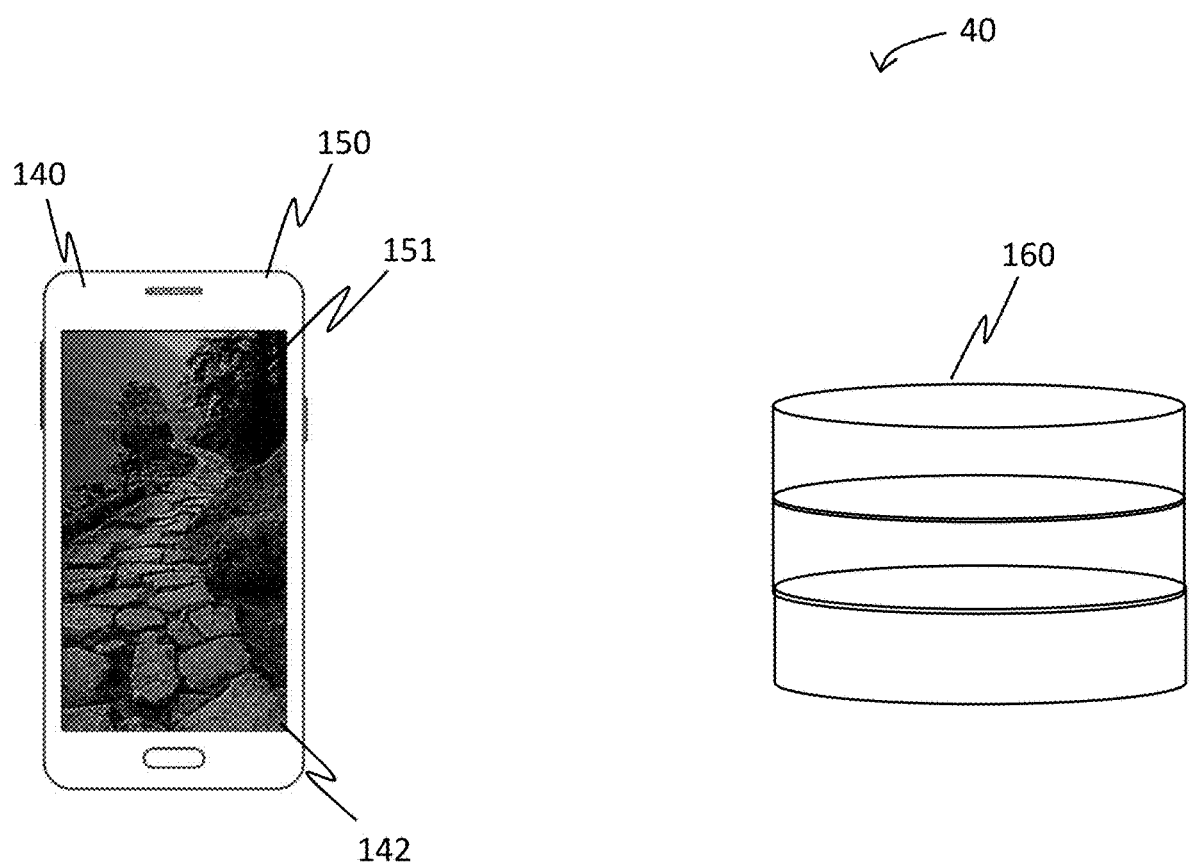
FIG. 4 is another view of the system designed for exercising while sitting of FIG. 1, according to an embodiment of the present disclosure.

FIG. 4 is another view of the system designed for exercising while sitting 100 of FIG. 1, according to an embodiment of the present disclosure. Here the mobile device application 150 on the mobile device 140 is in communication with an online database 160 where a user 40 registers a personal profile and chooses what virtual environment 151 to be shown on the digital display 142.

Figure 5:
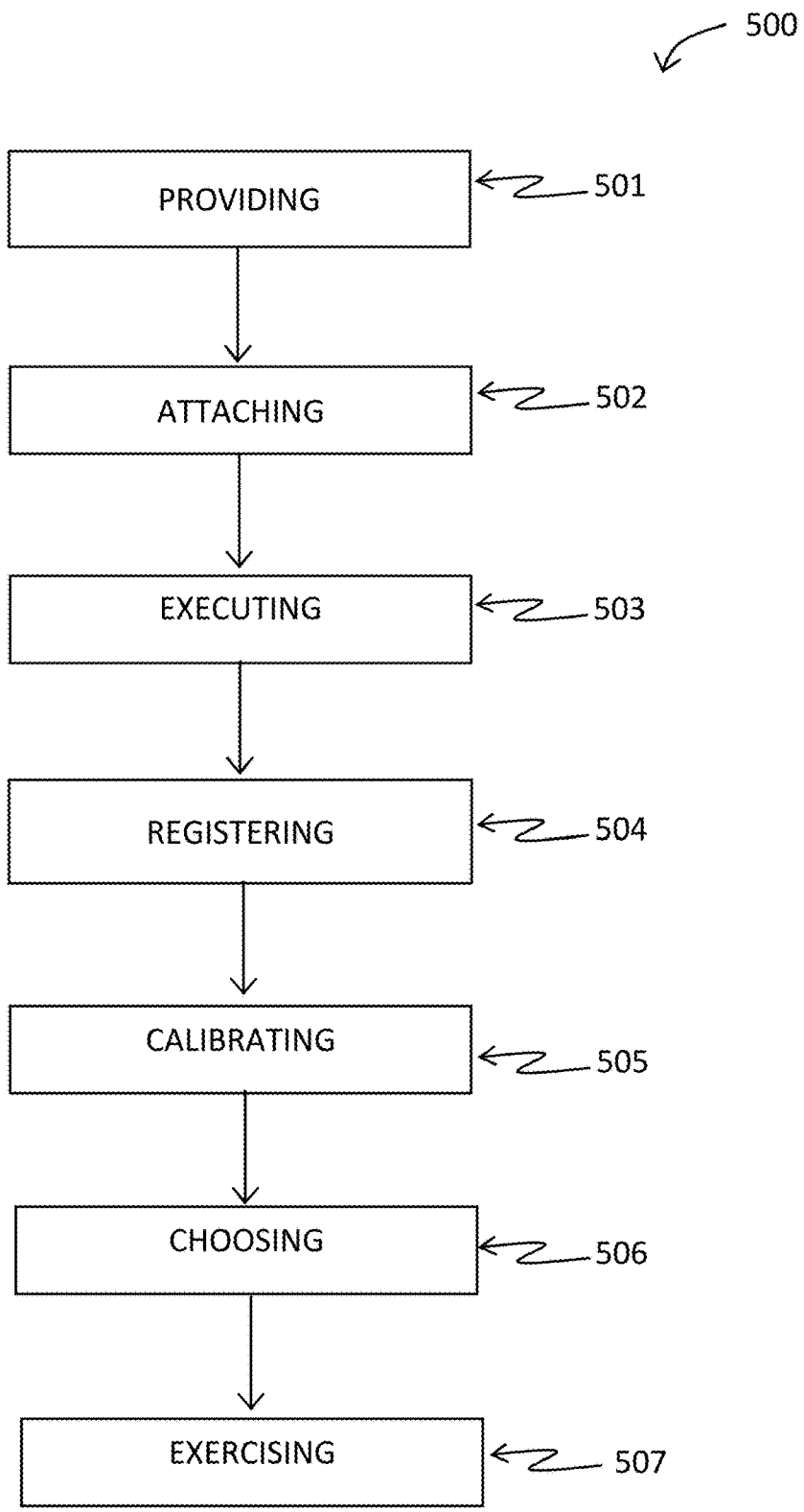
FIG. 5 is a flow diagram illustrating a method (of use) for exercising while sitting, according to an embodiment of the present disclosure.

Referring now to FIG. 5 showing a flow diagram illustrating a method for exercising while sitting 500, according to an embodiment of the present disclosure. In particular, the method (of use) for exercising while sitting 500 may include one or more components or features of the system designed for exercising while sitting 100 as described above. As illustrated, the method for exercising while sitting 500 may include the steps of: step one 501, providing a system designed for exercising while sitting, the system comprising a rigid housing having a first side configured to receive at least one piece of motion sensing hardware; at least one sensor configured to identify an oscillatory motion of a knee raising and lowering through pivoting of an ankle of the user wherein a heel of a foot of the user lifts off of a surface and wherein a toe of the user remains planted on the surface; a mobile device in wireless communication with the at least one sensor; a mobile device application installed on the mobile device configured to: register the user to the mobile device application; calibrate strokes of the oscillatory motion to a cycle counter of the mobile device application; calculate energy expended by the user from performing the oscillatory motion; and to display a virtual environment; step two 502, attaching a housing with the at least one sensor onto a knee of the user; step three 503, executing the mobile device application on a mobile device; step four 504, registering a profile with an online-database such that the user may review and resume progress from a saved point; step five 505, calibrating the oscillatory motion of the knee of the user such that the at least one sensor records the desired amplitude of motion; step six 506, choosing the virtual environment to transverse; and step seven 507, exercising through initiation of repetitive the oscillatory motion.

It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for exercising while sitting, are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A system designed for exercising while sitting, said system comprising:
   a rigid housing having a first side and a second side configured to receive at least one piece of motion sensing hardware;
   at least one sensor configured to secure to a knee of a user and identify an oscillatory motion of the knee raising and lowering through pivoting of an ankle of the user wherein a heel of a foot of said user lifts off of a surface and wherein a toe of said user remains planted on said surface;
   a mobile device in wireless communication with said at least one sensor, wherein the sensor is external to the mobile device;
   wherein the mobile device having a mobile device application stored thereon, the mobile device adapted to:
      calibrate each stroke of said oscillatory motion to a cycle counter of said mobile device application, wherein a single oscillatory motion of the knee raising and lowering through pivoting of the ankle of the user is equivalent to a single stroke;
      calculate energy expended by said user from performing said oscillatory motion; and
      display a virtual environment having a virtual route, wherein the virtual environment advances forward along the virtual route with each stroke.

2. The system designed for exercising while sitting of claim 1, wherein said rigid housing has a hook and loop fastener system disposed across the first side.

3. The system designed for exercising while sitting of claim 2, wherein said rigid housing further comprises an aperture configured to receive a plurality of USB connections.

4. The system designed for exercising while sitting of claim 3, wherein said at least one sensor is nested within said rigid housing.

5. The system designed for exercising while sitting of claim 4, wherein said at least one sensor is configured to sense elevation.

6. The system designed for exercising while sitting of claim 4, wherein said at least once sensor is configured to sense acceleration.

7. The system designed for exercising while sitting of claim 4, wherein said at least one sensor further comprises an energy source.

8. The system designed for exercising while sitting of claim 1, wherein said mobile device has internet communication capability.

9. The system designed for exercising while sitting of claim 1, wherein said mobile device has a digital display screen.

10. The system designed for exercising while sitting of claim 1, wherein data from processes of said mobile device application are sent to said mobile device by said at least one sensor.

11. The system designed for exercising while sitting of claim 1, wherein said mobile device application is in communication with an online-database.

12. The system designed for exercising while sitting of claim 11, wherein said user registers a profile onto said online-database.

13. The system designed for exercising while sitting of claim 1, wherein said mobile device application displays statistics related to said user performing said oscillatory motion.

14. The system designed for exercising while sitting of claim 1, wherein said mobile device application displays said virtual environment on a digital display screen.

15. The system designed for exercising while sitting of claim 1, wherein said mobile device application periodically provides hydration reminders to said user through visual indications on a digital display screen.

16. A system designed for exercising while sitting, said system comprising:
   a rigid housing having a first side and a second side configured to receive at least one piece of motion sensing hardware;
   at least one sensor configured to secure to a knee of a user and identify an oscillatory motion of the knee raising and lowering through pivoting of an ankle of the user wherein a heel of a foot of said user lifts off of a surface and wherein a toe of said foot of said user remains planted on said surface;
   a mobile device in wireless communication with said at least one sensor, wherein the sensor is external to the mobile device;
   a mobile device application installed on said mobile device configured to register said user to said mobile device application;
   wherein the mobile device application is adapted to:
      calibrate each stroke of said oscillatory motion to a cycle counter of said mobile device application, wherein a single oscillatory motion of the knee raising and lowering through pivoting of the ankle of the user is equivalent to a single stroke;
      calculate energy expended by said user from performing said oscillatory motion; and
      display a virtual environment having a virtual route, wherein the virtual environment advances forward along the virtual route with each stroke;
   wherein said rigid housing has a hook and loop fastener system disposed across the first side;
   wherein said rigid housing further comprises an aperture configured to receive a plurality of USB connections;
   wherein said sensor is nested within said rigid housing;
   wherein said at least one sensor is configured to sense elevation;
   wherein said at least once sensor is configured to sense acceleration;
   wherein said at least one sensor further comprises an energy source;
   wherein said mobile device has internet interaction capability;
   wherein said mobile device has a digital display screen;

wherein process data from said mobile device application is sent to said mobile device by said at least one sensor;
wherein said mobile device application is in communication with an online-database;
wherein said user registers a profile onto said online-database;
wherein said mobile device application displays statistics related to said user performing said oscillatory motion;
wherein said mobile device application displays said virtual environment of said digital display screen; and
wherein said mobile device application provides hydration reminders to said user through visual indications on said digital display screen.

17. A method for using a system designed for exercising while sitting, said method comprising:
providing a system designed for exercising while sitting, said system comprising:
a rigid housing having a first side configured to receive at least one piece of motion sensing hardware;
at least one sensor configured to secure to a knee of a user and identify an oscillatory motion of the knee raising and lowering through pivoting of an ankle of said user wherein a heel of a foot of said user lifts off of a surface and wherein a toe of said user remains planted on said surface;
a mobile device in wireless communication with said at least one sensor;
a mobile device application installed on said mobile device configured to register said user to said mobile device application;
sitting in a seat and attaching a housing with said at least one sensor onto a knee of said user;
executing said mobile device application on a mobile device;
registering a profile with an online-database such that said user may review and resume progress from a saved point;
displaying a virtual environment having a route on the mobile device;
detecting an amplitude of motion of the knee via the at least one sensor to calibrate each stroke of the oscillatory motion to a cycle counter of said mobile device application, wherein a single oscillatory motion of the knee raising and lowering through pivoting of the ankle of the user is equivalent to a single stroke;
remaining seated and repeating the stroke, wherein the virtual environment advances forward along the virtual route with each stroke.

* * * * *